United States Patent
Gruenbacher et al.

(10) Patent No.: US 6,547,468 B2
(45) Date of Patent: Apr. 15, 2003

(54) DOSING RESERVOIR

(75) Inventors: Dana Paul Gruenbacher, Fairfield, OH (US); Kevin Joe Fields, Irmo, SC (US); Dean Arthur Zimmerman, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/887,407

(22) Filed: Jun. 22, 2001

(65) Prior Publication Data

US 2002/0197094 A1 Dec. 26, 2002

(51) Int. Cl.[7] .................................................. B43K 5/14
(52) U.S. Cl. ............................. 401/133; 401/132; 604/3
(58) Field of Search ................................. 401/133, 132, 401/134, 135, 7; 604/3, 2, 1

(56) References Cited

U.S. PATENT DOCUMENTS

| | | |
|---|---|---|
| 2,209,914 A | 7/1940 | Gerber et al. |
| 2,779,465 A | 1/1957 | Anderson |
| 2,790,982 A | 5/1957 | Schneider |
| 3,053,385 A * | 9/1962 | Spees ........................ 401/132 |
| 3,196,478 A | 7/1965 | Baymiller et al. |
| 3,324,500 A | 6/1967 | Fuller et al. |
| 3,485,562 A | 12/1969 | Hidden et al. |
| 3,608,709 A | 9/1971 | Pike et al. |
| 3,635,567 A | 1/1972 | Richardson, Jr. |
| 3,636,922 A | 1/1972 | Ketner |
| 3,768,916 A | 10/1973 | Avery |
| 4,071,921 A | 2/1978 | Jury |
| 4,148,318 A | 4/1979 | Meyer |
| 4,430,013 A | 2/1984 | Kaufman |
| 4,475,835 A | 10/1984 | Verboom et al. |
| 4,510,640 A | 4/1985 | Omori |
| 4,537,819 A | 8/1985 | Schortmann et al. |
| 4,596,481 A | 6/1986 | Tanaka |
| 4,600,620 A | 7/1986 | Lloyd et al. |
| 4,613,446 A | 9/1986 | Magyar |
| 4,759,472 A | 7/1988 | Strenger |
| 4,762,124 A | 8/1988 | Kerch et al. |
| 4,775,372 A | 10/1988 | Wilberg |
| 4,878,775 A | 11/1989 | Norbury et al. |
| 4,935,018 A | 6/1990 | Scholz |
| 4,948,047 A | 8/1990 | Zembrodt |
| 4,951,657 A | 8/1990 | Pfister et al. |
| 4,998,671 A | 3/1991 | Leifheit |
| 5,090,832 A | 2/1992 | Rivera et al. |
| 5,318,504 A | 6/1994 | Edenbaum et al. |
| 5,320,217 A | 6/1994 | Lenarz |
| 5,380,110 A | 1/1995 | Festa |
| 5,454,207 A | 10/1995 | Storandt |
| 5,460,620 A | 10/1995 | Smith et al. |
| 5,487,889 A | 1/1996 | Eckert et al. |
| 5,490,736 A | 2/1996 | Haber et al. |
| 5,558,874 A | 9/1996 | Haber et al. |
| 5,562,642 A | 10/1996 | Smith et al. |
| 5,616,201 A | 4/1997 | Finch et al. |
| 5,681,574 A | 10/1997 | Haber et al. |
| 5,902,433 A | 5/1999 | Becher et al. |
| 5,962,011 A | 10/1999 | DeVillez et al. |
| 6,068,820 A | 5/2000 | De Guzman |
| 6,119,272 A | 9/2000 | Tebbe |
| 6,123,068 A | 9/2000 | Lloyd et al. |

FOREIGN PATENT DOCUMENTS

| | | |
|---|---|---|
| AU | A 15012/92 | 11/1993 |
| EP | 0 294 189 | 12/1988 |
| GB | 899016 | 6/1962 |
| GB | 924503 | 4/1963 |

* cited by examiner

*Primary Examiner*—David J. Walczak
(74) *Attorney, Agent, or Firm*—Peter D. Meyer

(57) ABSTRACT

A dosing reservoir for distributing an active compound in controlled amounts onto a target surface comprising a first impermeable layer and a second permeable layer facing and affixed to the first layer. A fluid tight cell with a frangible seal and containing an active compound is disposed between the first and second layers. When the frangible seal is ruptured, the active compound is released from the cell and is controllably released from the reservoir through the permeable layer.

18 Claims, 6 Drawing Sheets

DOSING RESERVOIR

FIELD OF THE INVENTION

The present invention relates to a dosing reservoir useful for distributing an active compound in controlled amounts onto target surfaces. More particularly, the present invention relates to dosing reservoirs wherein the substance may be dosed to an applicator material, released from the applicator material and distributed upon the surface of a target object.

BACKGROUND OF THE INVENTION

Disposable articles comprising a capsule filled with an active composition and an absorbent material upon which the active composition is distributed, are representative of various articles to which the present invention is applicable. When the article is needed for use, the user breaks the capsule and spreads its contents onto the absorbent material. The user then applies the absorbent material to the surface to be treated. These capsules do not allow for controlled, dosed release of the active composition.

For example, U.S. Pat. No. 4,878,775, issued to Norbury, et al., discloses an applicator comprising a burstable microcapsule containing a liquid active. Pressure on the device breaks the capsule, delivering all entrained active within the capsule through the permeable sheet. Norbury does not provide for the controlled release for the capsule entrained active.

U.S. Pat. No. 3,768,916, issued to Avery, discloses a scrubbing device comprised of a sponge with a hollow portion in which a frangible ampule containing a liquid soap is inserted. The user breaks the ampule, dispensing the contained soap en masse into the sponge substrate. Avery does not provide for the controlled release for the ampule-entrained soap solution.

U.S. Pat. No. 5,090,832, issued to Rivera, et al., discloses a disposable pad comprising a packet of cleaning material that ruptures and saturates a scrubber layer. Rupturing of the packet results in the unregulated flow of the packet contents to the scrubber layer. Rivera does not control the release of the cleaning material from the packet.

European Patent Number EP 294,189, issued to Moloney, discloses a flexible bag combined with an absorbent applicator. Again, the flexible bag is ruptured, releasing the contents of the flexible bag in an uncontrolled fashion onto the absorbent applicator.

German Patent Number DE 3,545,926, issued to Frühauf, discloses a system utilizing non-rupturable capsules sandwiched between two sealed layers. Delamination of the seal under pressure causes the contents of the capsule to free-flow outward. Logically, the delamination is not predictable, resulting in the uncontrolled release of the entrained agent.

Moreover, the use of such articles frequently results in exposure of a user's hands to the substance. At the very least such a scenario results in a waste of product and is undesirable from an aesthetic standpoint. Accordingly, it would be desirable to provide a dosing reservoir useful for distributing substances in controlled amounts to a target surface. It would also be desirable to provide an applicator incorporating a dosing reservoir to distribute a substance in a controlled manner to a target surface.

SUMMARY OF THE INVENTION

The present invention relates to a dosing reservoir for controllably releasing an active compound onto target surfaces comprising a first impermeable layer, a second permeable layer facing and affixed to the first layer. A fluid tight cell containing an active compound is disposed between the first and second layers. The fluid tight cell has a frangible seal to release the active compound. The released active compound is then controllably released from the dosing reservoir through the permeable layer.

The present invention also relates to a dosing reservoir for distributing an active compound in controlled amounts to a target surface comprising a first fluid impermeable cell, a second fluid permeable cell in communication with the first cell, and a frangible seal separating the first and second cells.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements, reference numerals with the same final two digits identify corresponding elements, and wherein:

DETAILED DESCRIPTION OF THE INVENTION

The present invention is related to a dosing reservoir for distributing an active compound in controlled amounts to a target surface. The dosing reservoir comprises a first impermeable layer and a second permeable layer affixed to the first layer. The dosing reservoir contains a fluid tight cell containing an active compound having a frangible seal to release the active compound placed between the first and second layers. The active compound is then controllably released from the reservoir through the permeable membrane.

The invention is more generally related to a dosing reservoir comprising a first fluid impermeable cell, a second fluid permeable cell in communication with the first cell. A frangible seal separates the first cell and the second cell.

Benefits provided by such dosing reservoirs include an easy to use and low cost means for the delivery of a controlled amount of lotion or fluid to virtually any surface. These benefits can be directed to a multitude of user-beneficial outcomes including, but not limited to polishing, cleaning, and/or rubbing, bleaching, cooling, heating, deodorizing, disinfecting, medicating, and wiping. Optionally, but preferably, the present invention features a support material designed to transport the active compound upon release. This support material is designed to assist the user in the application of the product.

The Reservoir

Figure 1:
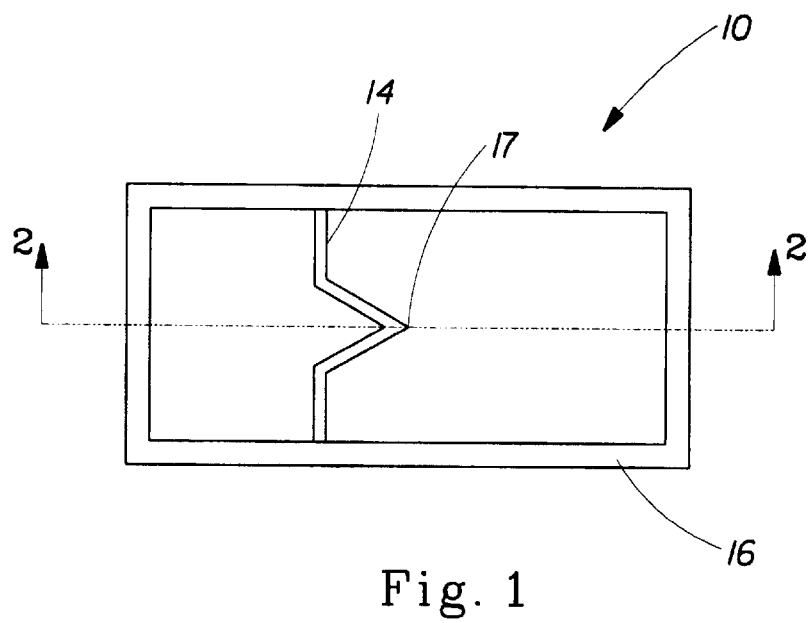
FIG. 1 is a plan view of a preferred embodiment of a dosing reservoir in accordance with the present invention.
Figure 2:
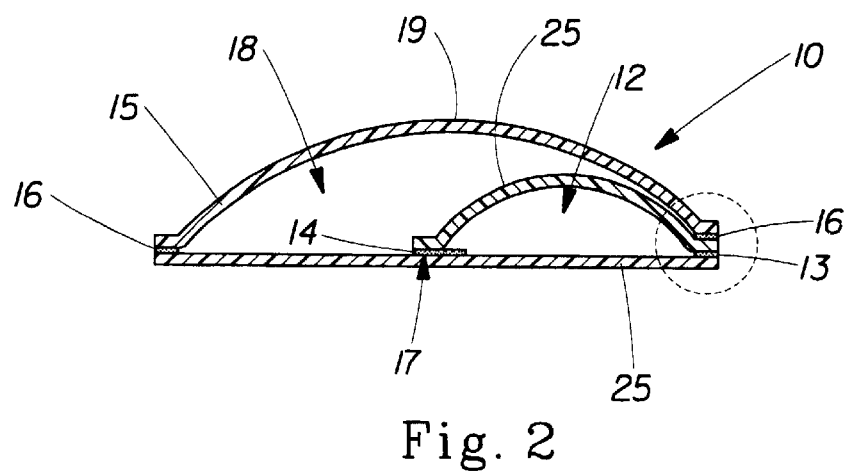
FIG. 2 is a cross-sectional view of the dosing reservoir of FIG. 1 taken along line 2—2.

Shown in FIGS. 1 and 2, dosing reservoir 10 (reservoir) contains an active compound that contains an active compound that may be dispensed and/or dispersed from a cell 12 to one or more outer surfaces 19 of reservoir 10, for delivery to a target surface. Cell 12 may be of any suitable size, configuration, and composition for the active compound to be dispensed and dispersed, for example, planar. The active compound may be a liquid, a gel, a lotion, a cream, a powder or even a solid. A solid such as a wax, for example, may be heated to provide a flowable product that may be dispensed and/or dispersed from cell 12. One aspect of cell 12, which is believed to be important to the overall functionality of dosing reservoir 10, is the ability of cell 12 to rupture or otherwise dispense a contained active compound when "activated" by the user, and yet, resist premature dispensing during manufacture, packaging, and shipment. The ability of reservoir 10 to survive intact until the point of use preserves the quality and quantity of active compound until the time of use.

As best shown in FIGS. 1 and 2, dosing reservoir 10 is made from a flexible film 25 sealed around the perimeter by permeable membrane 15. In a non-limiting example, cell 12 can be formed from a single material partially or completely folded onto itself. The folded material is then heat sealed on at least three sides. Cell 12 can then contain the active compound as discussed in detail below. Cell 12 can also be made by sealing two films to each other along a common perimeter. Flexible film 25 can include a sealant on one or both sides and can include a higher melting support structure such as a thin layer of PET, nylon, or polypropylene. Seals 13 that create cell 12 can be both permanent seals, such as such as lock-up or welded seals, or have a rupturable or frangible capacity.

Figure 2A:
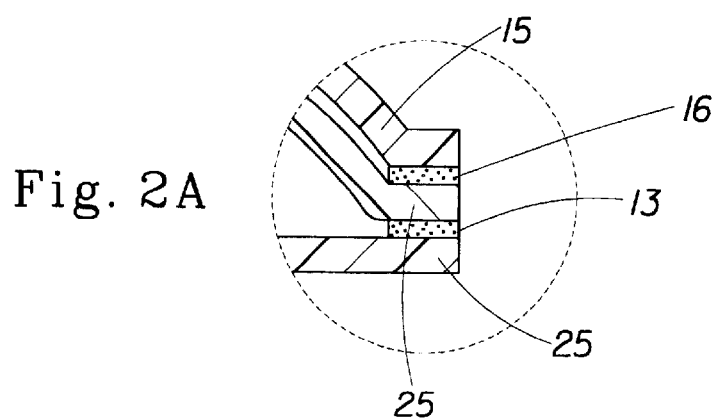
FIG. 2A is an expanded view of the region labeled 2A in FIG. 2.

In one embodiment according to FIGS. 2 and 2A, cell 12 can be designed to burst or rupture to release active compound at a comparatively low force, e.g., finger or hand pressure, when desired. This may be accomplished by having a sealing system with permanent seals 13, 16 and frangible seal 14. "Frangible" means rupturable and yields a release of active compound into second cell 18. Seals 13, 16 are permanent seals that do not rupture when force is applied to the dosing reservoir 10 or cell 12. When reservoir 10 is squeezed, frangible seal 14 yields or fails first since it has a lower peel force to break the seal apart than seals 13, 16. In one embodiment, frangible seal 14 will ideally rupture with 0.5–10 pounds (2.23–44.5 Newtons (N)), more preferably 1–4 pounds (4.45–17.8 N) of applied force. Stress concentrator 17 in the seal geometry of frangible seal 14 can localize forces, optimizing the rupture location. Stress concentrators 17 can be shaped like a V, a notch, a half circle or a variety of other shapes depending upon the desired burst strength. Stress concentrators 17 can help control the force required to burst cell 12 as well as the location of where frangible seal 14 ruptures. For example, pressurizing reservoir 10 having a V-notch seal as shown in FIG. 2 can localize forces mainly at the apex of the V, causing that region to rupture first. This can help reduce variability in rupture or dispensing forces and the location where the rupture occurs.

In FIGS. 2 and 2A, permeable membrane 15 is sealed to the perimeter of flexible film 25 with seals 16 that also seal over seal 13. This can be accomplished by producing flexible film 25 to be heat sealable on both sides. The sealant layers can ideally have different seal temperatures so that seal 16 is made at a lower temperature than seal 13.

In FIG. 2, reservoir 10 includes cell 12, frangible seal 14, and at least one permeable membrane 15. Cell 12 can be in a fixed or unfixed relationship with membrane 15. Cell 12 can be formed from two impermeable layers forming a cavity. A third layer comprising permeable membrane 15 is coextensive with the first two layers and forms a cavity with the second layer. Frangible seal 14 is disposed between the first and second layer to allow deposition of an active compound proximate to membrane 15. The embodiment of FIG. 2 can be made by peripherally joining two similarly-sized and shaped pieces of fluid-impervious material with seals 13, forming a dispensing aperture in one portion of at least one of the pieces of material, introducing the product through the aperture, and then forming frangible seal 14 of limited strength to separate cell 12 from membrane 15 from the aperture. Other non-limiting forming techniques, such as folding a single piece of material double upon itself and sealing, or rolling and sealing a sleeve of material, can be utilized.

Reservoir 10 can have a cell 12 comprised of multiple chambers for mixing incompatible products. This could allow delivery of superior performance at an affordable cost. As a non-limiting example, one chamber could contain a skin cleansing solution, and the other chamber could contain a skin moisturizing oil. Alternatively, several formulations can be dosed sequentially to deliver superior performance.

A material for making cell 12 is defined as a flexible film 25. Such a material is defined as having a permeation of less than 10% product loss/year at 35° C./20% RH, so that the active compound maintains its designed activity. This can be achieved by using a film which is: liquid impervious in that no liquid passes through it after 30 sec.; a barrier to vapors/solvents in that its water vapor transmission rate (WVTR) is less than 6 g/sqm/day at 40° C./90% RH; and optionally a barrier to gases, in that its $O_2TR$ (oxygen transmission rate) is less than 200 cc/sqm/day/atm at 23° C./50% RH.

Cell 12 preferably uses a laminate film or multi-layer structure that contains either metallized PET, aluminum foil, $SiO_2$ or other high barrier material. In a most preferred embodiment, the film is laminated comprising at least one aluminum layer that gives very good barrier properties to liquids, gas and vapors, for example, a Surlyn®/metallized PET/LDPE having thicknesses of 50 μm/12 μm/24 μm respectively. Optionally, thermoplastics, such as high-density polyethylene (HDPE) more than 50 μm thick, or polypropylene (PP) more than 100 μm thick, or low-density polyethylene (LDPE) more than 150 μm thick can be used. Even if such materials are not inherently high barrier materials, the thickness used allows good barrier properties.

Figure 3:
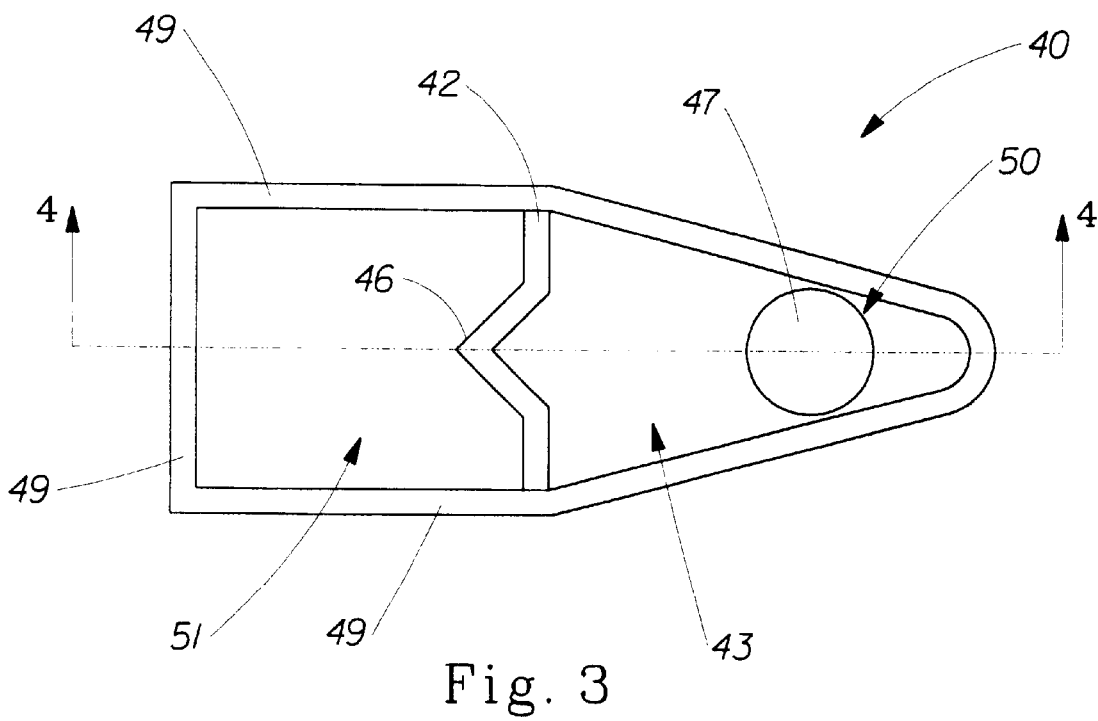
FIG. 3 is a plan view of another embodiment of a dosing reservoir.
Figure 4:
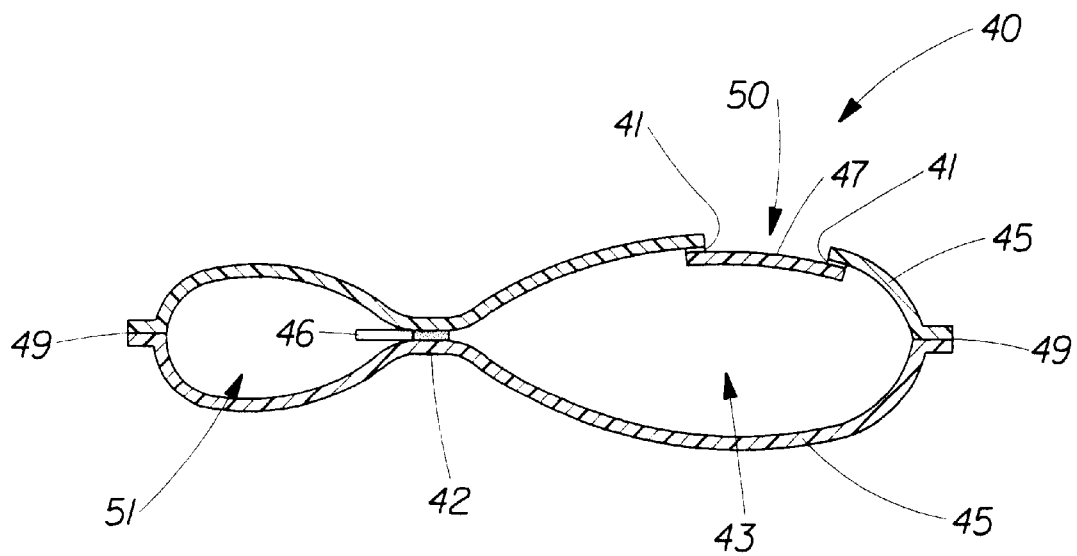
FIG. 4 is a cross-sectional view of the dosing reservoir of FIG. 3 taken along line 4—4.

Alternatively, FIGS. 3 and 4 show an exemplary dosing reservoir 40 with permanent seals 49 and frangible seal 42. Seals 49 are permanent seals that do not rupture when force is applied to reservoir 40. Cell 51 is preferably formed from two layers having permanent seals 49 and frangible seal 42 to thereby contain an active compound. When cell 51 is squeezed, frangible seal 42 yields causing active compound to enter the second permeable cell 43. Stress concentrator 46 can localize the applied force at a particular location within the geometry of frangible seal 42. Membrane 47 is sealed to flexible film 45 around its perimeter with seals 41. This can be accomplished by producing the flexible film to be heat sealable on both sides. The sealant layers can ideally have different temperatures so that seal 41 is made at a lower temperature than permanent seals 49.

The Frangible Seal

In one first embodiment according to FIG. 1, cell 12 can be made frangible by a number of different techniques. One preferred technique is to make cell 12 on a vertical or horizontal form/fill/seal machine that has the ability to make different seals on cell 12 at different temperatures, pressures or seal times. This allows one side of cell 12 to have different sealing conditions that in turn can allow one side to have weaker seal strengths. A suitable sealant material for this type of frangible seal is an ionomer, such as Surlyn®, blended with an incompatible material such as polybutylene (PB) or polypropylene (PP), a blend of ethylene vinyl acetate (EVA) with PB, ultra low density ethylene copolymers, polyolefin plastomers, and/or polyethylene. Sealant layers made with any of these resins or blends results in a sealant layer that will have significantly different seal strengths depending upon the seal temperature. Surlyn® is preferred as a base resin due to the seal provided through liquid contamination during the cell sealing process. The polybutylene/Surlyn® blend provides a "contaminant" to the base polymer material that allows the resulting seal to be selectively frangible under certain sealing conditions. For example, at 93° C., 40 psi (2.72 atm), 0.5 sec, the sealant layer can provide a peel force of from about 5–50 grams/linear centimeter (g/cm) of seal width, and more preferably 10–30 g/cm. At 150° C., 40 psi (2.72 atm), 0.5 seconds, the seal can provide a peel force greater than 90 g/cm, more preferably 180 g/cm, and most preferably greater than 270 g/cm of seal width. This variation in seal strength allows a cell to be "welded" shut in one region and frangible in a second region by adjusting the seal temperature, the seal time and/or the seal pressure used when making the cell seals (e.g., the cell may be welded along all or a portion of one, two, three or more sides and easily burstable along a portion of one, two, three or more sides). A preferable film structure would be Surlyn® with PB/tie layer/metallized PET/LDPE. Frangible seals can also include: delaminating seals, weakening the film structure by embossing, laser scoring, mechanical scoring or forming small thermoformed cells with thin regions that rupture when squeezed (similar to bubble wrap).

The Dosing Package

Dosing reservoir 10 has a membrane 15 as shown in FIGS. 1 and 2. Membrane 15 is specified to have a permeability that will release an active compound through membrane 15 at the desired rate given a net pressure head. Without wishing to be bound by theory, membrane permeability will depend upon the viscosity and surface energy properties of the active compound. The flow rate through membrane 15 can be controlled by varying the thickness of membrane 15, the number of openings in membrane 15, or the size of these openings so that fluid can travel through membrane 15.

Without attempting to be limiting, membranes such as those of the present invention can be made from apetured films, non-wovens, non-wovens with microfibers, wovens, meltblown structures, and combinations thereof, or other flexible materials known to those skilled in the art to control fluid flow. As used herein, the term microfibers means small diameter fibers having an average diameter not greater than about 100 $\mu$m, for example, having a diameter of about 0.5 $\mu$m to about 50 $\mu$m, more specifically microfibers may also have an average diameter of from about 1 $\mu$m to about 20 $\mu$m. Microfibers having an average diameter of about 3 microns or less are commonly referred to as ultra-fine microfibers. Non-woven membranes made with microfibers can allow for thinner substrates since smaller effective pores can be created.

The hole size of the apertured film can be between 20 $\mu$m to 500 $\mu$m, more preferably 50 $\mu$m to 200 $\mu$m and the number of holes can be adjusted to change the net flow rate as would be known to those with skill in the art. The porosity for non-wovens, wovens, and meltblown structures can be controlled by the basis weight (thickness) of the structure as well as the mean fiber diameter. The number and size of the fibers essentially creates pores where fluid can occupy space and change flow rate for a given pressure. Suitable meltblowns have been shown to have a basis weight range from 2 gsm to 30 gsm, thus, basis weight can be used to adjust porosity and thus flow rate.

According to FIG. 2, the product release area can also be controlled by varying the total area of membrane 15. This restricts the region where active compound can be released. Alternatively, membrane 15 can be treated in areas with coatings that restrict fluid flow through those coated regions or, vice versa, to encourage fluid flow through those regions.

The flow rate through membrane 15 can be controlled by coating membrane 15 with an extruded hot melt film or barrier coating. Still yet another approach is to apply a hydrophilic or hydrophobic coating that prevents membrane 15 from becoming wetted in predetermined regions. Alternatively, membrane 15 can be coated in regions that encourage fluid flow with a substance that assists the membrane with wetting. Alternatively, dosing reservoir 40 can have a membrane 47 as shown in FIGS. 3 and 4. Here, cell 43 is formed from two layers of flexible film having permanent seal 49. Permanent seal 41 seals membrane 47 into opening 50 of cell 43. Thus, when frangible seal 46 ruptures, active compound is released into cell 43 and then controllably dispensed from membrane 47.

Cell Contents

In preferred embodiments, the contents of cell 12 of the present invention may be suitable for application to the skin, hair, or nails of humans or animals, which means that the composition and its components are suitable for use in contact with skin, hair, and nails without undue toxicity, incompatibility, instability, allergic response, and the like within the scope of sound medical judgment. Such active compounds are comprised of a single or plurality of ingredient components, and may include a topically active compounds or combination of active compounds. The formulation of such compositions forms no part of this invention. The following materials are given simply by way of exemplification. These active compounds may include, but are not limited to: conventional ingredients such as alcohols, colorants/pigments, emollients, emulsifiers, oils, polymers, waxes, and the like depending on the product type, and can be routinely chosen by one skilled in the art for a given product type. *The CTFA Cosmetic Ingredient Handbook*, Second Edition (1992), herein incorporated by reference, describes a wide variety of non-limiting cosmetic and pharmaceutical ingredients commonly used in the skin care industry, which are suitable for use in the composition of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, methyl lactate witch hazel distillate), anti-acne agents, anti-caking agents, anti-foaming agents, anti-fungal agents, anti-inflammatory agents, anti-microbial agents (e.g., iodopropyl butylcarbamate), antioxidants, anti-wrinkle agents, binders, biological additives, buffering agents, bulking agents, chelating agents, chemical additives, colorings/colorants, cosmetic astringents, cosmetic biocides, denaturants, desquamation actives, drug astringents, external analgesics, film formers or materials, e.g., polymers, for aiding the film-forming properties or substantivity of the composition (e.g., copolymer of eicosene and vinyl pyrrolidone), opacifying agents, pH adjusters, reducing agents, sequestrants, skin bleaching and lightening agents (e.g., hydroquinone, kojic acid, ascorbic acid, magnesium ascorbyl phosphate, ascorbyl glucosamine), skin coloring or tanning agents, skin-conditioning agents (e.g., humectants, including miscellaneous and occlusive), skin-soothing and/or healing agents (e.g., panthenol and derivatives, e.g., ethyl panthenol), aloe vera, pantothenic acid and its derivatives, allantoin, bisabolol, and dipotassium glycyrrhizinate), skin-treating agents, sunscreens, thickeners, and vitamins and derivatives thereof.

In any embodiment of the present invention, however, the active compound useful herein can be categorized by the benefit they provide or by their postulated mode of action. However, it is to be understood that the active compound useful herein can in some instances provide more than one benefit or operate via more than one mode of action. Therefore, classifications herein are made for the sake of convenience and are not intended to limit the active compound to the particular application.

Preferred Properties of Product a) Viscosity

Active compounds suitable for use in the present invention may cover a broad range of viscosities, so long as the active compound either readily flows or can otherwise be dispensed or discharged from cell 12 by a squeezing action or other external pressure applied on the dosing reservoir 10 by the user. In particular, they may range from low viscosity liquids (e.g., water) to high viscosity liquids, emulsions, mousses, gels, or pastes, on the order of several hundred to several hundred thousand centipoise. While not wanting to be limiting, products with a shear-thinning or thixotropic behavior are particularly well-suited to the present invention, benefiting from the shear stresses produced on the product by the application of external pressure to the reservoir and/or the act of rubbing dispensed product from the applicator onto a target surface.

b) Product Integrity

Cell 12 of the present invention is particularly well suited to protect and maintain the integrity of the preferred active compound. This integrity may take the form of protection from microbiological contamination, oxidation, evaporation, or moisture. Protection from oxidation is especially valuable in sustaining the efficacy of many active ingredients (e.g., making cell 12 opaque for Vitamin A active).

The Support Material

Figure 5:
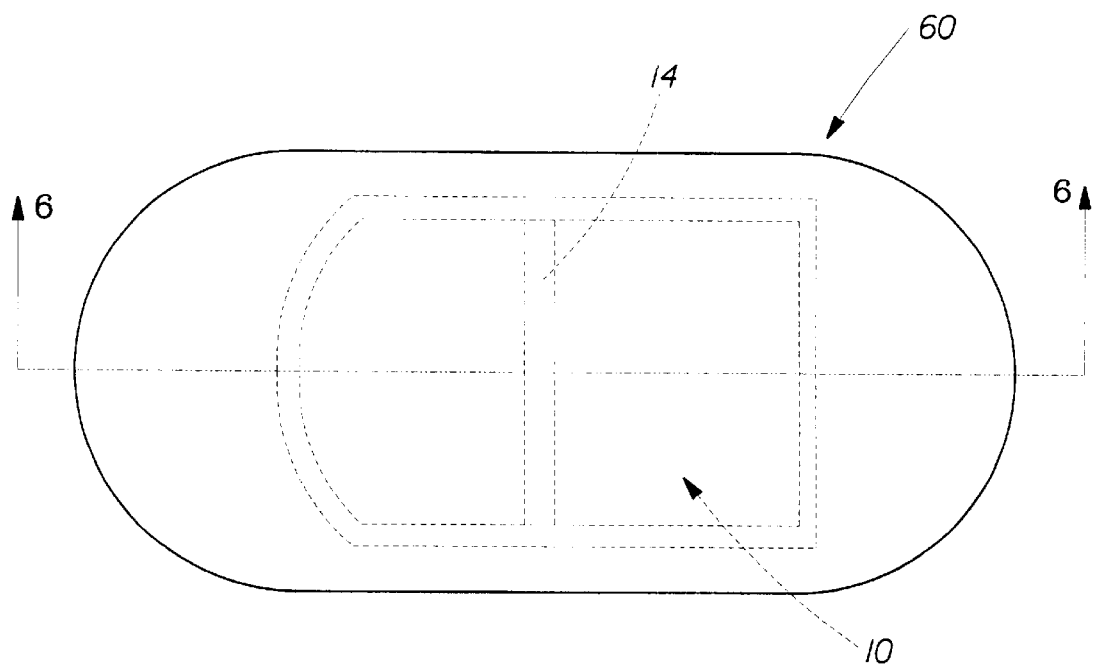
FIG. 5 is a plan view of a preferred embodiment of an applicator utilizing the dosing reservoir of FIG. 1 in accordance with the present invention.
Figure 6:
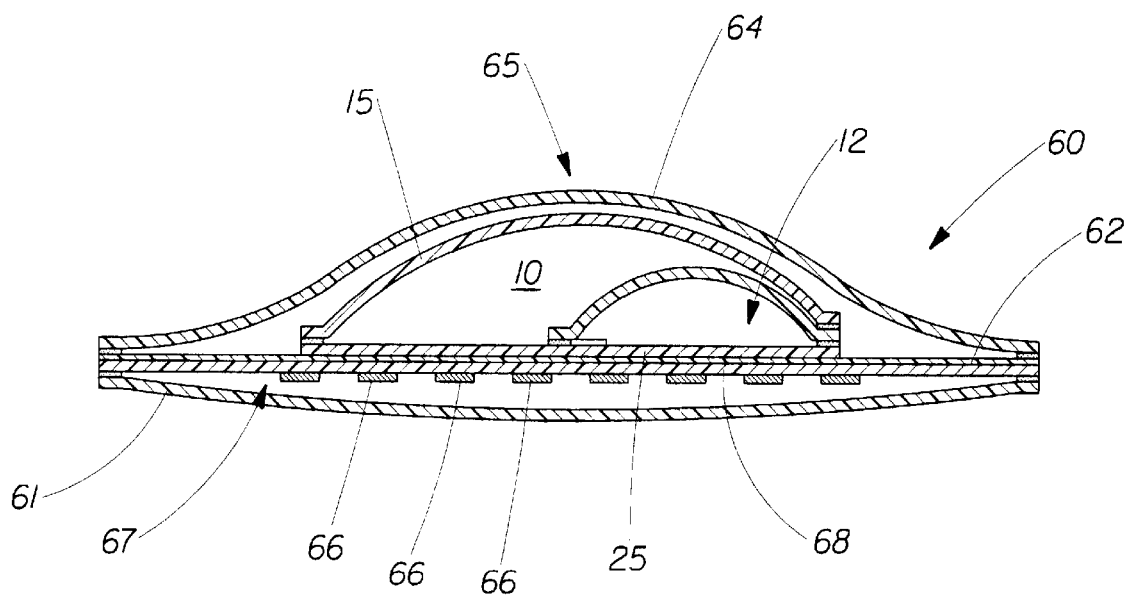
FIG. 6 is a cross-sectional view of the applicator of FIG. 5 taken along line 6—6.

In FIGS. 5 and 6, the coupling of reservoir 10 to barrier layer 62 and dispensing material 64 forms applicator 60. Applicator 60 can have a smooth surface for pampering, a rough surface for cleaning, rubbing or removing dead skin for example, or can be spongy for moisturizing/impregnating a surface. The thickness, shape and dimensions of material 64 should be chosen in relation to the number of cells 12 inside dosing reservoir 10, and the volume of active compound contained inside each cell 12. Material 64 may be comprised of a synthetic woven, synthetic knit, knit and durable fabrics, woven fabrics, nonwoven, absorbent or fibrous absorbent materials, or laminates or combinations thereof. The nonwovens may be made by, but not limited to, any of the following methods: spunlaced, spunbond, meltblown, bonded carded, hydroapertured, hydroentangled or hydraulically entangled, carded, air through bonded, calendar bonded, or combinations thereof.

Reservoir 10 can be used as a single applicator or can be combined into a pad, mitt, or wipe form that allows the use of additional layers to help with holding onto the pouch and/or improving application. Applicator 60 preferably has a layer 68 that provides a soft, easy to hold surface. Affixed to layer 68 is barrier layer 62 that prevents active compound from wetting layer 68 keeping opposing layers dry. Layer 62 can also direct product towards the application side 65 of applicator 60. Reservoir 10 can be sealed between layer 62 and material 64. Material 64 can be a non-woven, woven, paper, tissue, film, or any combination thereof and known to those skilled in the art that has the desired applicator side properties. This can include a non-woven that is soft and feels cloth-like but also does not retain product. A polyethylene non-woven such as a 60 gsm spun bond LLDPE or LDPE made by BBA under the brand name Corolind® has been shown to have good softness and acceptable release properties. In most instances, material 64 is preferably non-absorbent or contains a low percentage of absorbent fibers, has a thinner basis weight with limited voids to retain less than 60 percent, more preferably, 40 percent, and most preferably, 20 percent of the active compound in cell 12.

As shown in FIG. 6, a strap, grab-tab, or additional layer 66 can be sealed to the perimeter of the back side of layer 68 to further aid in holding applicator 60. Layer 66 can provide a higher friction surface for holding applicator 60 and for example, a high coefficient of friction Kraton®-based coating. In this form, a user slides a hand between layer 68 and strap 61 with the palm facing layer 68.

Still another embodiment seals permeable membrane 15 to layer 62 around the perimeter of dosing reservoir 10. In this embodiment, permeable membrane 15 is not sealed to flexible film 25, but creates a reservoir between membrane 15 and baffler layer 62 rather than between membrane 15 and flexible film 25. This allows the use of a continuous layer of membrane to make applicators where membrane material 15 is unwound in the applicator making process. This arrangement can be used with or without an applicator 60.

Manufacture

An exemplary process to make the reservoir 10 of FIG. 1 involves a vertical form/fill/seal machine that has independent temperature and preferably pressure control for each seal. Seal 13 is sealed at a higher temperature than seal 16. Folding flexible film 25 so an overlap results provides a region where the inside surface of flexible film 25 can be sealed to membrane 15. A conventional forming shoulder used in most vertical form/fill/seal equipment can be used to fold flexible film 25. Beneath the forming shoulder is a filling tube that is used to fill cell 12 with an active compound. Seal 14 is ideally made prior to filling cell 12 with active to allow seal 14 to occur with less risk of liquid contamination. Flexible film 25 is then advanced to the next station where some of seals 13 are made. At this time, cell 12 is partially formed so that an active compound can be dispensed into cell 12 and seal 13 is then made. In some cases, seal 13 is through the active compound to provide minimal headspace. After cell 12 has been formed, membrane 15 is sealed to flexible film 25 around the perimeter of cell 12 at seal locations 16 to form dosing reservoir 10. Dosing reservoir 10 is then placed onto a conveyor for combination into an applicator such as a wipe, pad, mitt, glove, or other form.

Figure 7:
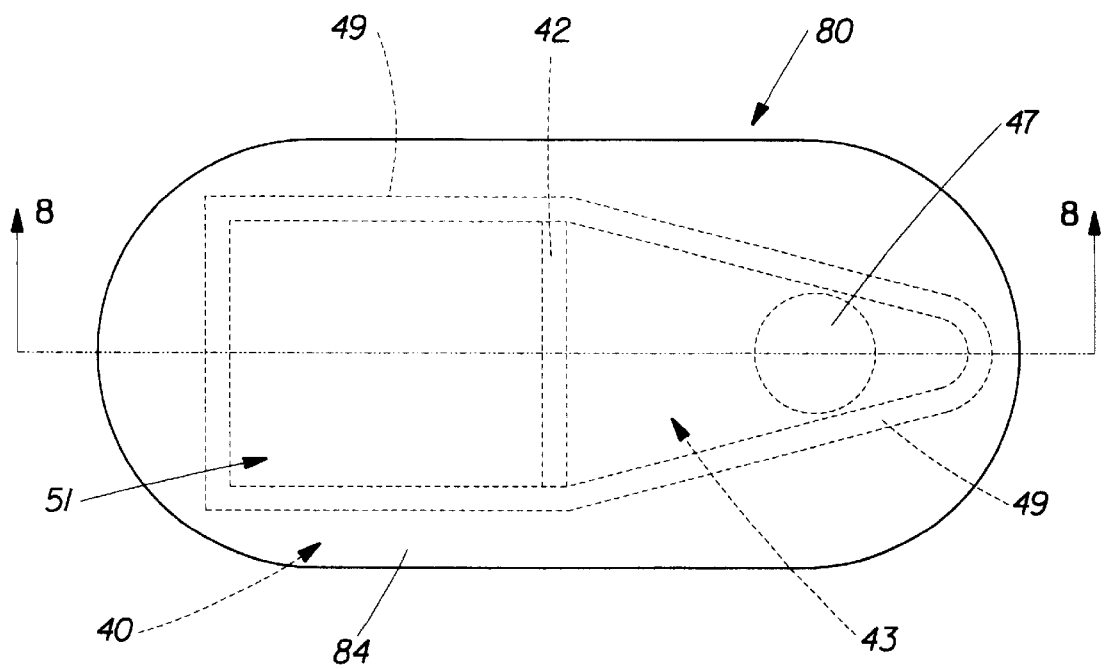
FIG. 7 is a plan view of another embodiment of an applicator.
Figure 8:
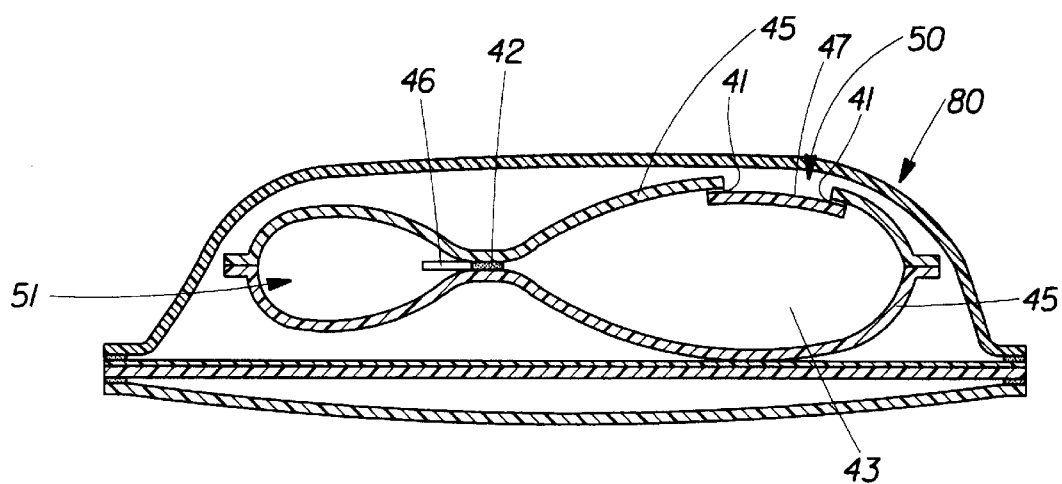
FIG. 8 is a cross-sectional view of the applicator of FIG. 7 taken along line 8—8.

Alternative configurations of the invention can be made to release active compound through a small area or a large area, for example, releasing active compound through a small area as shown in FIGS. 7 and 8. Membrane 47 is sealed to cell 43 with seals 41 on the inside or outside of flexible film 45 to cover an opening 50 die-cut out of flexible film 45 prior to folding. This allows active compound to be dispensed through membrane 47 in a very controlled manner over a small area that would be suitable for spot treating or applying active compound to the face. For example, opening 50 can be shaped to allow the user to get very close to the area surrounding the eyes. Applicator 80 can be made to fit over one or more fingers and can have a back strap or additional layers sealed to back side (not shown).

EXAMPLES

Different possible embodiments of applicators comprising a dosing reservoir according to the present invention will now be described in detail, with reference to the accompanying figures.

Example 1

An applicator made in accordance with the present invention as shown in FIGS. 5 and 6, can include a body lotion pad. The same pad could also be used to dispense sunscreen lotion, medications, insect repellant or any lotion to be applied to skin. The pad is constructed with a dosing reservoir made from a flexible film that comprising 0.5 mil (12 $\mu$m) LDPE/48 gauge metalized PET/1.0 mil (24 $\mu$m) metallocene-catalyzed PE/0.75 mil (18 $\mu$m) Surlyn® AD8273. This reservoir is heat sealable on both sides and maintains flexibility and softness for skin contact. The sealant layer for creating the lotion-containing dosing reservoir is formed from the Surlyn® composite. The LDPE sealant layer is used to bond a permeable membrane to the flexible film. Maintaining the Surlyn® side internal, the reservoir is formed by folding the flexible film onto itself, leaving a region that forms a flap.

Reservoir 10 is formed with permanent seals 13, 16 and frangible seal 14 as described previously and would be known to one skilled in the art. In this case, permanent seals 13, 16 are formed at a lower temperature than frangible seal 14. When using Surlyn® AD8273, two different bond strengths result. In this example, the frangible seal was made at 100° C., 2.7 atm pressure, and 0.6 seconds of seal time while the permanent seals were produced at 150° C., 2.7 atm and 0.6 seconds yielding a peel strength of 6.6 N for a one inch (2.5 cm) seal width. The frangible seal had a 2.2 N peel strength for a one inch (2.5 cm) seal width. Other sealants such as polybutylene blended with EVA, polyethylene (PE), polypropylene (PP), or Surlyn® may also yield consistent peelable and lock-up seals depending upon the sealing temperature. The membrane is two layers of 100 mesh hydro-apetured, low-density polyethylene (LDPE) film made by Tredegar®. The membrane is sealed around the perimeter of the dosing reservoir. The reservoir is sealed between a 60 gsm spunbond LLDPE made by BBA Corporation (Corolind®) and a 1 mil LDPE barrier film. An additional layer may be added to provide a softer and easier to hold pad. The layer in this example was a 150 gsm thermally bonded air-laid non-woven comprised of cellulose and thermoplastic fibers and was made by Concert, Inc. A laminate of 30 gsm PE/PP bi-component non-woven/2 mil (48 $\mu$m) of elastomer (Tredegar VFE X-27222)/30 gsm PE/PP that has been run through an adhesive bonding process and activated by incremental straining. A soft elastic strap was used to keep the pad on the hand.

Example 2

A finger applicator was constructed for applying liquid foundation to the face. The applicator was constructed with a flexible film comprised of a sealant layer laminated to 8 $\mu$m metalized PET for moisture, oxygen, and perfume barrier with a coating of 18 $\mu$m polypropylene on the surface. The sealant layer was 24 $\mu$m thick and was a blend of 75% low-density polyethylene and 25% polybutylene. This sealant layer has properties that allow a stable, peel seal strength from about 100 to 140 degrees C. and higher seal strengths at 160–180 degrees C. This allows the formed reservoir to be sealed with lock-up seals and frangible seals. The reservoir of FIG. 4 was made by cutting a 0.5 inch (1.25 cm) diameter opening in the form of a circle 50 in the flexible film near the end of one side of film. A membrane 47 was then sealed to the inside surface of flexible film. The membrane 47 was a 4 gsm meltblown polypropylene comprising a continuous strip of material ¾ inch (1.9 cm) wide. The seal 41 was produced by heat sealing the membrane over the opening producing a seal 1.3 cm inside diameter and 1.9 cm outside diameter. Folding a flexible film in half at a central fold line formed the reservoir. The frangible seal 42 was formed by sealing the film at 100° C. for 0.6 seconds at 2.7 atm. The permanent seals 49 were then made at 170° C. The permanent seals 49 extend along the bottom of the reservoir, around the reservoir opening, leaving an opening at the top of the reservoir to allow product to be filled. The reservoir was then filled with 5 cm$^3$ of Cover Girl® liquid foundation manufactured by The Procter & Gamble Company.

After filling reservoir 51 with liquid, the frangible seal 42 is made at the same conditions as the permanent seals. The reservoir 51 was filled to a level such that there was minimal air headspace and the thickness was approximately 0.5 to 0.75 cm. This can allow the pouch to be easily ruptured when the reservoir is squeezed. The applicator was then folded along frangible seal 42 to protect the frangible seal from rupturing as would be realized by one skilled in the art.

Example 3

Figure 9:
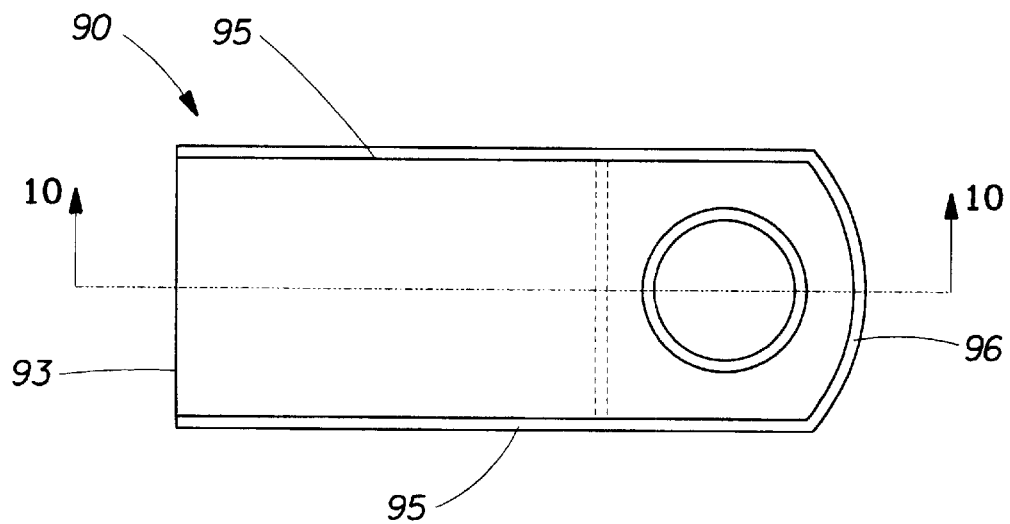
FIG. 9 is a plan view of another embodiment of a dosing reservoir.
Figure 10:
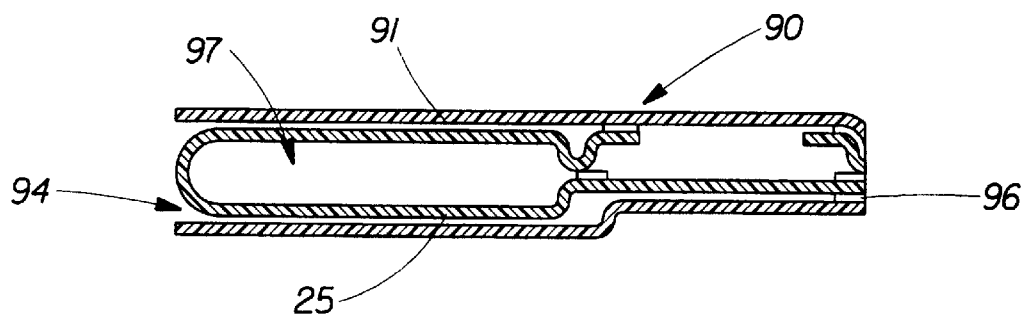
FIG. 10 is a cross-sectional view of the dosing reservoir of FIG. 9 taken along line 10—10.

An applicator 90 was turned into a finger-mitt for premium application and ease of use by applying layers of non-woven material on either side of applicator. As shown in FIGS. 9 and 10, a 60 gsm LLDPE non-woven material 91 was sealed to the perimeter of applicator 90, on the lotion release side. The seals were made on top of seals 95, 96 as well as edge 93. The seals were made by sealing the LLDPE to the 12 $\mu$m layer of PP on the outer surface of flexible film

25. The LLDPE non-woven provides a soft surface for applying a liquid foundation to the face. On the back of applicator 90, an elastic strap material to hold the applicator 90 to the finger was fixably attached by sealing. The strap was sealed along seals 95, 96, but not along edge 93, leaving opening 94 for a finger to be inserted. Thus, a user could slide the finger mitt over finger, press reservoir 97 with a thumb and proceed to apply liquid foundation to their face with application surface 91.

Example 4

A pad for applying stain to wood furniture was constructed as shown in FIGS. 5 and 6 by making a reservoir 12 as shown in FIG. 6 and filling reservoir 12 with 25 cm$^3$ of MinWax® brand Gel stain. Membrane 15 was an 8 gsm polypropylene meltblown non-woven. Top substrate material 64 was a 60 gsm hydroentangled nonwoven comprised of rayon, cellulose, and PET fibers. This substrate is both absorbent and hence will resist dripping as well as somewhat abrasion resistant. A 1-mil (24 $\mu$m) layer of polyethylene film was used as barrier layer 62 to protect the hand and keep the stain from going towards the cavity in which the hand is inserted. Layer 62 in this example was a 0.008 cm thick layer of Kraton® film laminated to an air-laid ring rolled PE non-woven. Layer 62 covers the entire backside of applicator 60 and was sealed around the perimeter except for one side that left the opening 67 for the hand to occupy. The elastic Kraton® film provided a barrier layer to keep the stain from getting on the hand as well as provides an elastic strap 61 to keep applicator 60 from falling off the hand. The air-laid PE non-woven provides a soft substrate for the inside to keep hand from sweating and to provide better air circulation.

Example 5

Figure 11:
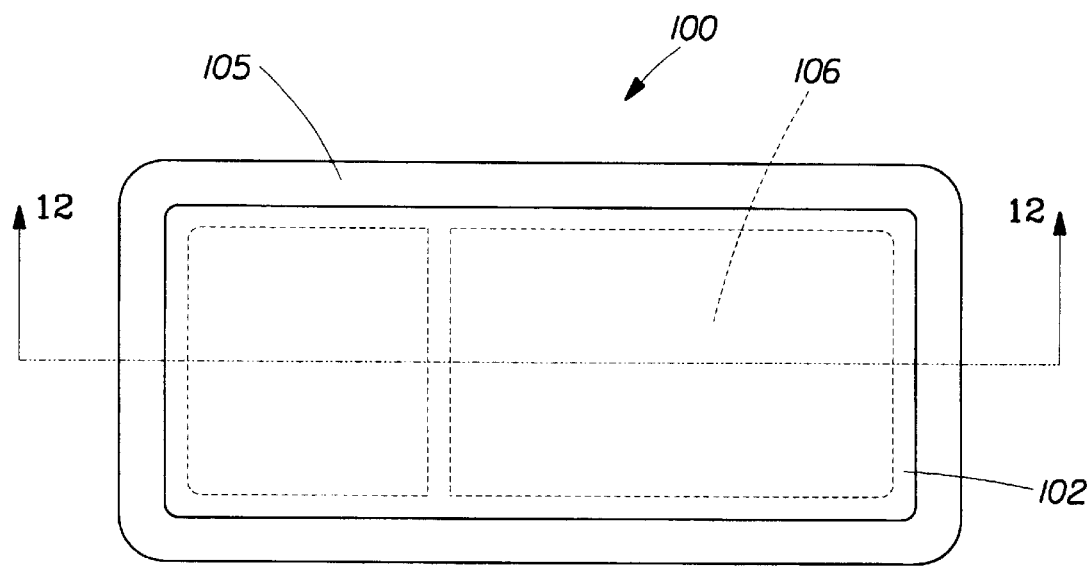
FIG. 11 is a plan view of another embodiment of an applicator.
Figure 12:
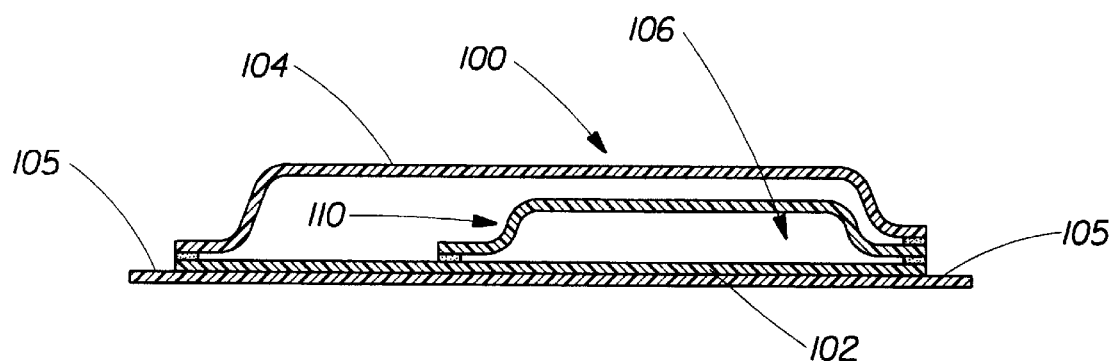
FIG. 12 is a cross-sectional view of the dosing reservoir embodiment of FIG. 11 taken along line 12—12.

Another example provides a pad for releasing medication to a skin surface. A slow release medicine applicator 100 was constructed as shown in FIGS. 11 and 12. A barrier layer of 1 mil (24 $\mu$m) polyethylene 102 was coated with a hydrogel body adhesive 105 from the 3M Corporation. Attached in the center of pad 100 was dosing applicator 110. Reservoir 106 was filled with 2 cm$^3$ of a mixture of an active ingredient.

In use, the applicator would be covered with a release liner that would cover the exposed surface of adhesive 105. The user then removes the release liner and sticks applicator 100 over the treatment area. Reservoir 106 can be ruptured before attaching to skin or by application of a downward force on the reservoir of 9–18 N. The medicine is then released through the entire surface of membrane 104. This medication pad can be used for virtually any transdermal system for releasing drugs such as Scopolamine, Nitroglycerin, Clonidine, skin healing drugs, biologicals, or combinations thereof.

While particular embodiments of the present invention have been illustrated and described, it will be obvious to those skilled in the art that various changes and modifications may be made without departing from the spirit and scope of the invention. One skilled in the art will also be able to recognize that the scope of the invention also encompasses interchanging various features of the embodiments illustrated and described above. Accordingly, the appended claims are intended to cover all such modifications that are within the scope of the invention.

What is claimed is:
1. A dosing reservoir comprising:
   (a) a first impermeable layer;
   (b) a second permeable layer facing and affixed to said first layer;
   (c) a fluid tight cell containing an active compound disposed between said first and second layer;
   (d) said fluid tight cell having a frangible seal to release said active compound; and,
   wherein said active compound is controllably released from said reservoir through said permeable layer.
2. The dosing reservoir of claim 1 wherein said dosing reservoir is generally planar.
3. The dosing reservoir of claim 1 wherein said fluid tight cell is held in fixed relation between said first and second layers.
4. The dosing reservoir of claim 1, wherein said first layer is a multi-layered structure.
5. The dosing reservoir of claim 1, wherein said frangible seal is selected from the group consisting of a polybutylene/EVA blend, polypropylene/ionomer blend, polybutylene/ionomer blend, ultra-low density ethylene copolymers, polyolefin plastomers, PE, and combinations thereof.
6. The dosing reservoir of claim 1, wherein said frangible seal has a peel force of from about 5 grams per linear centimeter to about 50 grams per linear centimeter.
7. The dosing reservoir of claim 1, wherein said permeable membrane is an apertured film having apertures range from about 20 $\mu$M to about 500 $\mu$M.
8. The dosing reservoir of claim 1, wherein said permeable membrane is coated with a hydrophilic or hydrophobic agent.
9. The dosing reservoir of claim 1, further comprising:
   (e) an applicator medium for at least partially containing said dosing reservoir.
10. A dosing reservoir comprising:
   (a) a first fluid impermeable cell;
   (b) a second fluid permeable cell in communication with said first cell; and,
   (c) a frangible seal separating said first cell and said second cell;
   wherein an active compound contained within said first fluid impermeable cell is transported to said second fluid permeable cell in response to an application of a force to said first fluid impermeable cell, said force rupturing said frangible seal; and
   wherein said active compound is controllably released from said second fluid permeable cell.
11. The dosing reservoir of claim 10 wherein said first cell further comprises:
   (a) a first layer; and,
   (b) a second layer facing said first layer and forming a cavity therebetween; and,
   (c) an active compound within said cavity.
12. The dosing reservoir of claim 10 wherein said second permeable cell further comprises:
   (a) a first layer; and,
   (b) a second layer comprising a permeable membrane facing said first layer and forming a cavity therebetween.
13. The dosing reservoir of claim 12, wherein said permeable membrane is an apertured film having apertures ranging from about 20 $\mu$M to about 500 $\mu$M.
14. The dosing reservoir of claim 10 wherein said frangible seal has a peel force of from about 5 grams per linear centimeter to about 50 grams per linear centimeter.

15. The dosing reservoir of claim 10, wherein said permeable membrane is coated with a hydrophilic or hydrophobic agent.

16. The dosing reservoir of claim 10 further comprising:
(d) an applicator medium for at least partially containing said dosing reservoir.

17. A dosing reservoir comprising:
(a) a first layer;
(b) a second layer facing said first layer and forming a first cavity therebetween;
(c) a third layer comprising a permeable membrane facing said second layer and forming a second cavity therebetween; and,
(d) a frangible seal disposed between said first layer and said second layer;

wherein an active compound disposed within said first cavity is released to said second cavity in response to a force rupturing said frangible seal; and wherein said active compound is controllably released from said second cavity through said permeable membrane.

18. The dosing reservoir of claim 17, wherein said third layer is co-extensive with said first layer and said second layer.

* * * * *

UNITED STATES PATENT AND TRADEMARK OFFICE
CERTIFICATE OF CORRECTION

PATENT NO. : 6,547,468 B2
DATED : April 15, 2003
INVENTOR(S) : Dana Paul Gruenbacher et al.

It is certified that error appears in the above-identified patent and that said Letters Patent is hereby corrected as shown below:

Column 8,
Line 54, "baffler" should be -- barrier --

Signed and Sealed this

Fourteenth Day of September, 2004

JON W. DUDAS
*Director of the United States Patent and Trademark Office*